United States Patent
Shaw et al.

(10) Patent No.: US 9,975,867 B2
(45) Date of Patent: May 22, 2018

(54) SYNTHETIC PROCESS FOR PREPARING 2-FUROIC ACID DERIVATIVES

(71) Applicant: Dermira Inc., Menlo Park, CA (US)

(72) Inventors: Anthony Adrian Shaw, Menlo Park, CA (US); Kanjai Khumtaveeporn, Aurora (CA); Pavel Krasik, Aurora (CA)

(73) Assignee: Dermira Inc., Menlo Park, CA (US)

( * ) Notice: Subject to any disclaimer, the term of this patent is extended or adjusted under 35 U.S.C. 154(b) by 55 days.

(21) Appl. No.: 15/015,569

(22) Filed: Feb. 4, 2016

(65) Prior Publication Data

US 2016/0229825 A1    Aug. 11, 2016

Related U.S. Application Data

(60) Provisional application No. 62/112,519, filed on Feb. 5, 2015.

(51) Int. Cl.
  *C07D 307/68*    (2006.01)
(52) U.S. Cl.
  CPC .................. *C07D 307/68* (2013.01)
(58) Field of Classification Search
  None
  See application file for complete search history.

(56) References Cited

U.S. PATENT DOCUMENTS

| | | |
|---|---|---|
| 4,110,351 A | 8/1978 | Parker |
| 8,884,034 B2 | 11/2014 | Daynard et al. |
| 2010/0204317 A1 | 8/2010 | Hunt et al. |

FOREIGN PATENT DOCUMENTS

DE    40 33 563 A1    4/1992

OTHER PUBLICATIONS

Carraher, C., Synthesis of Furfuryl Alcohol and Furoic Acid, 1978, Journal of Chemical Education, vol. 55, No. 4, pp. 269-270.*
Manly et al., Simple Furan Ethers. II: 2-Alkoxy- and 2-Aryloxy-furans, 1956, J. Org. Chem., 21(5), pp. 516-519.*
Khrouf et al., Polyesters bearing furan moieties. Part 3. A kinetic study of the transesterification of 2-furoates as a model reaction for the corresponding polycondensations, 1999, Polym Int, 48, pp. 649-659.*
Guseva et al., "TOFA (5-tetradecyl-oxy-2-furoic acid) reduces fatty acid synthesis, inhibits expression of AR, neuropilin-1 and Mcl-1 and kills prostate cancer cells independent of p53 status," *Cancer Biology & Therapy* 12(1):80-85, Jul. 2011.
Mandel et al., "Synthesis of spiroketals under neutral conditions via a type III ring-rearrangement metathesis strategy," *Chem. Commun.* 47:10284-10286, 2011.
Parker et al., "5-(Tetradecyloxy)-2-furancarboxylic Acid and Related Hypolipidemic Fatty Acid-Like Alkyloxyarylcarboxylic Acids," *Journal of Medicinal Chemistry* 20(6):781-791, 1977.

\* cited by examiner

*Primary Examiner* — Kortney L. Klinkel
*Assistant Examiner* — Tori Strong
(74) *Attorney, Agent, or Firm* — Seed IP Law Group LLP

(57) ABSTRACT

Disclosed herein are processes for forming 2-furoic acid derivatives represented by Formula (I):

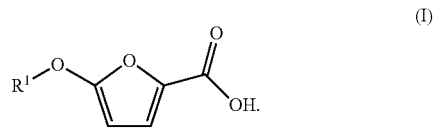

15 Claims, No Drawings

SYNTHETIC PROCESS FOR PREPARING 2-FUROIC ACID DERIVATIVES

CROSS-REFERENCES TO RELATED APPLICATION

This application claims the benefit under 35 U.S.C. § 119(e) of U.S. Provisional Patent Application No. 62/112,519, filed Feb. 5, 2015, which application is incorporated herein by reference in its entirety.

BACKGROUND

Technical Field

This disclosure is generally related to a synthetic process for preparing 2-furoic acid derivatives with improved yields and scalability.

Background

Fatty acid synthesis starts with the carboxylation of acetyl CoA to malonyl CoA. This irreversible reaction is the committed step in fatty acid synthesis. The synthesis of malonyl CoA is catalyzed by acetyl CoA carboxylase (ACC) (See, Brownsey, R. W. et al., "Regulation of acetyl-CoA carboxylase", Biochem Soc. Trans. (2006) 34: 223-227).

Inhibition of ACC can be effective in diminishing fatty acid synthesis. Long-chain (16-20 carbons) fatty acid acyl-CoA thioesters have been found to be potent physiological end-product inhibitors of mammalian ACC.

Certain 2-furoic acid derivatives, including those substituted with long chain alkoxides ($C_{12-20}$) are fatty acid mimetics. They can be converted intracellularly to their acyl-CoA thioesters, thus inhibiting ACC activity with a mechanism similar to long chain fatty acid acyl-CoA thioesters. See, McCune, S. A. et al., J. Biol. Chem. (1979), Vol. 254, No. 20. pp. 10095-10101.

TOFA (5-(tetradecyloxy)-2-furoic acid) is a known hypolipidemic compound having the following structure:

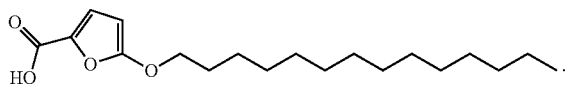 [SMILES: CCCCCCCCCCCCCCOc1ccc(C(=O)O)o1]

TOFA has been shown to reduce plasma triglyceride levels in both rats and monkeys. See, e.g., Parker, R. A. et al., J. Med. Chem. (1977), Vol. 20, pp. 781-791. It has also been known to inhibit hepatic fatty acid synthesis. See, e.g., Ribereau-Gayon, G., FEBS Lett. (1976), Vol. 62, No. 309-312; Panek, E. et al., Lipids (1977), Vol. 12, pp. 814-818; Kariya, T. et al., Biochem. Biophys. Res. Commun. (1978), Vol. 80, pp. 1022-1024; and Harris, R. A. et al., Hormones and Energy Metabolism (Klachko, D. M. et al., eds.), Vol. III, pp. 17-42. TOFA is further known to inhibit sebaceous gland disorders by lowering sebum production. See, e.g., U.S. Published Patent No. 2010/0204317, and German Patent No. 40 33 563.

TOFA has poor bioavailability through the skin. On the other hand, certain TOFA prodrugs have been found to be particularly effective against a range of dermatological disorders including acne vulgaris, acne conglobata, choracne, rosacea, Rhinophyma-type rosacea, seborrhea, seborrheic dermatitis, sebaceous gland hyperplasia, Meibomian gland dysfunction of facial rosacea, mitogenic alopecia, and oily skin. See U.S. Pat. No. 8,884,034, in the name of Dermira (Canada) Inc.

As an active pharmaceutical agent and an important precursor to other pharmaceutical agents, TOFA is commercially available at gram-scale quantities (e.g., Cedarlane Laboratories Inc.) and can be prepared according to the process described in Parker R. A. et al (Supra). However, the known procedures do not scale well and can only produce TOFA at low yields. Thus, there is a need to modify the synthetic approach to produce TOFA and related 2-furoic acid derivatives at improved yields and scalability.

BRIEF SUMMARY

One embodiment provides a process for preparing a compound of Formula (I)

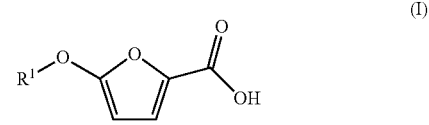

comprising:

converting a compound of Formula (II) to an intermediate compound of Formula (III):

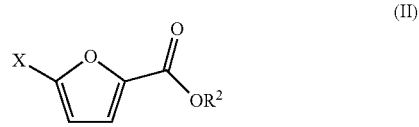

and saponifying the intermediate compound of Formula (III), wherein, $R^1$ is alkyl, aryl, aralkyl, cycloalkyl, cycloalkylalkyl, heteroaryl, heteroarylalkyl, heterocyclyl or heterocyclylalkyl; $R^2$ is $C_{1-4}$ alkyl; and X is halo.

In a further embodiment, converting the compound of Formula (II) to the intermediate of Formula (III) comprises:

transesterifying the compound of Formula (II) with $R^1$—OH to form an intermediate compound of Formula (IV):

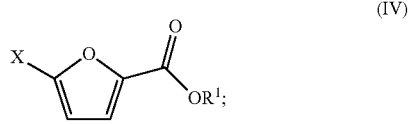

and converting the intermediate compound of Formula (IV) to the intermediate compound of Formula (III) in the presence of $R^1$—OH and a base.

Yet another embodiment provides a composition comprising a compound of Formula (III) and a base, which has a conjugate acid having a pKa value of at least 15, wherein the compound of Formula (III) is:

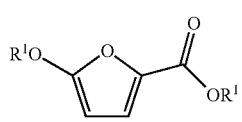

wherein, $R^1$ is alkyl, aryl, aralkyl, cycloalkyl, cycloalkylalkyl, heteroaryl, heteroarylalkyl, heterocyclyl or heterocyclylalkyl.

DETAILED DESCRIPTION

Described herein includes a process for preparing TOFA and related 2-furoic acid derivatives with improved yields (e.g., >70%) at lower temperatures compared to conventional TOFA synthesis. Also described is a composition comprising a reaction intermediate and a base.

Conventional TOFA Synthesis

TOFA is conventionally prepared by reacting 5-bromo-2-furoic acid with 1-tetradecanol ($C_{14}H_{29}OH$) under a basic condition, shown in the following reaction scheme:

Known Reaction Scheme

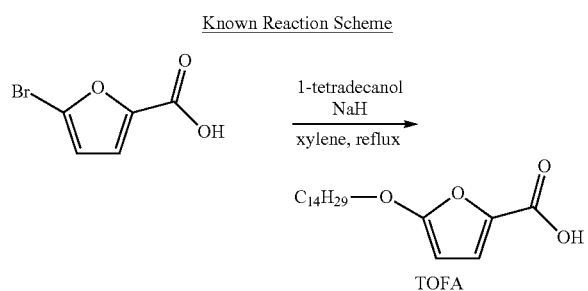

More specifically, the conventional procedure involved the preparation of 2.5 equivalents of sodium tetradecoxide by treating 1-tetradecanol with sodium hydride in oil and heating in refluxing xylenes (around 130-140° C.). To this mixture was added one equivalent of 5-bromo-2-furoic acid and the resulting mixture was heated under reflux for 42 hours. The mixture was cooled and diluted with diethyl ether and neutralized with 10% acetic acid. The organic layer was separated, washed with water and dried over anhydrous sodium sulfate. After removing the diethyl ether by distillation and cooling the xylene solution, the precipitate was collected and recrystallized in 2-butanone to afford TOFA in 46% yield. See also Parker R. A. et al (Supra).

The known synthetic approach requires high temperatures and produces TOFA at yields lower than 50%, which low yield cannot be maintained when scaling up.

Synthesis of 2-Furoic Acid Derivatives

According to an embodiment of the present disclosure, a 2-furoic acid derivative of Formula (I) can be prepared at low temperature (<80° C.) with high overall yield (e.g., about 85%)

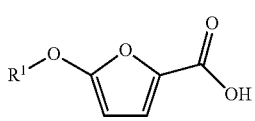

As shown in the General Reaction Scheme, the process begins with a 2-furoic acid ester reactant of Formula (II) and generates a symmetrically substituted alkoxy 2-furoic acid alkyl ester intermediate of Formula (III). The intermediate of Formula (III) is then saponified to a 2-furoic acid derivative of Formula (I). The generation of the intermediate of Formula (III) may involve a transesterification step to produce an intermediate of Formula (IV).

General Reaction Scheme

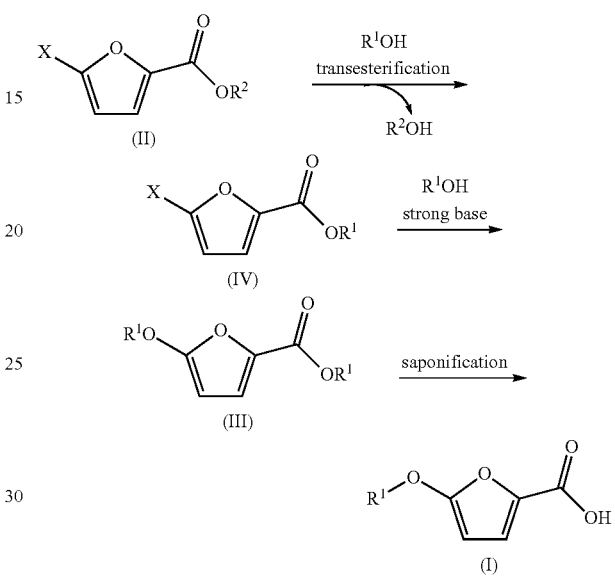

Advantageously, intermediates of Formulae (III) and (IV) need not be isolated before proceeding to the next steps. The entire process can proceed with much higher yield despite having two extra steps when compared to the known reaction scheme.

Thus, one embodiment provides a synthetic process for preparing 2-furoic acid derivatives represented by Formula (I)

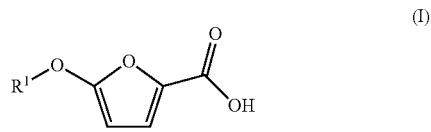

comprising:
converting a compound of Formula (II) to an intermediate compound of Formula (III):

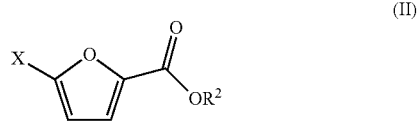

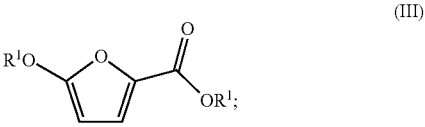

and
saponifying the intermediate compound of Formula (III), wherein,

R$^1$ is alkyl, aryl, aralkyl, cycloalkyl, cycloalkylalkyl, heteroaryl, heteroarylalkyl, heterocyclyl or heterocyclylalkyl;

R$^2$ is C$_{1-4}$ alkyl; and

X is halo.

Of this embodiment, converting the compound of Formula (II) to the intermediate compound of Formula (III) comprises:

transesterifying the compound of Formula (II) with R$^1$—OH to form a compound of Formula (IV)

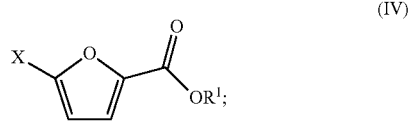

and converting the compound of Formula (IV) to the intermediate compound of Formula (III) in the presence of R$^1$—OH and a base.

The starting material, i.e., a halo-substituted 2-furoic acid ester compound of Formula (II) may be commercially available or be prepared by known methods in the art.

In certain embodiments, the starting material undergoes a transesterification with R$^1$—OH with simultaneous removal of a reaction by-product, i.e., R$^2$—OH.

In one embodiment, the removal of R$^2$—OH may be carried out in the presence of a Lewis acid in a refluxing aromatic solvent (e.g., toluene or benzene). As the by-product alcohol (R$^2$—OH) is being contemporaneously removed, the transesterification can proceed at 100% yield to form the intermediate of Formula (IV).

Suitable Lewis acids include transition metal alkoxides. In a preferred embodiment, the Lewis acid is titanium tetraisopropoxide.

The intermediate of Formula (IV) may proceed, without purification, directly to a substitution reaction with an alkoxide R$^1$O$^-$ to provide the alkoxy 2-furoic acid ester intermediate of Formula (III). The alkoxide R$^1$O$^-$ may be added by first combining R$^1$OH with a base. Alternatively and preferably, the alkoxide R$^1$O$^-$ may be formed in situ by adding a base to an excess amount of R$^1$—OH from the transesterification step. In particular, the transesterification may be carried out by using slightly more than 2 equivalents (e.g., 2.5 eq) of R$^1$—OH, thus leaving about 1.5 eq of unreacted R$^1$—OH for forming the alkoxide R$^1$O$^-$.

In various embodiments, the base is a strong base whose conjugate acid has a pKa of at least 15. Suitable bases include metal alkoxides, metal hydrides, and the like. In specific embodiments, the base may be potassium t-butoxide, sodium t-butoxide, potassium t-pentoxide, or sodium t-pentoxide. In a preferred embodiment, the base is potassium t-butoxide.

Advantageously, by starting the reaction with a 2-furoic acid ester (as opposed to 2-furoic acid), the formation of the alkoxy 2-furoic acid ester intermediate can be carried out rapidly at a low temperature (e.g., below 60° C. or even below 50° C.).

In various embodiments, the alkoxy 2-furoic acid ester intermediate of Formula (III), without being isolated or purified, undergoes a saponification step (or hydrolysis) to convert to the 2-furoic acid derivative of Formula (I) in the presence of a base. Typically, a base (e.g., a metal hydroxide) combined with an alcohol is preferred. In a specific embodiment, the base is potassium hydroxide combined with methanol.

The saponification step can be carried out at low temperature, i.e., below 50° C. Preferably, the temperature is in a range of 30-35° C.

In the above embodiments, R$^1$ may preferably be C$_{10-20}$ alkyl. In a particularly preferred embodiment, R$^1$ is —C$_{14}$H$_{29}$.

In another specific embodiment, R$^2$ is methyl.

In yet other embodiments, X is Br or Cl. In a preferred embodiment, X is Br.

In a preferred embodiment, the compound of Formula (I) prepared is 5-tetradecyloxy-2-furoic acid (TOFA).

Another embodiment provides a composition of a compound of Formula (III) and a base.

In certain embodiments, the base may be a strong base whose conjugate acid has a pKa of at least 15. Suitable bases include metal alkoxides, metal hydrides, and the like. In specific embodiments, the base may be potassium t-butoxide, sodium t-butoxide, potassium t-pentoxide, or sodium t-pentoxide.

In a preferred embodiment, the base is potassium t-butoxide.

In a preferred embodiment, the compound of Formula (III) is

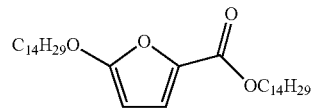

Definitions

Certain chemical groups named herein may be preceded by a shorthand notation indicating the total number of carbon atoms that are to be found in the indicated chemical group. For example; C$_7$-C$_{12}$alkyl describes an alkyl group, as defined below, having a total of 7 to 12 carbon atoms, and C$_4$-C$_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Amino" refers to the —NH$_2$ radical.

"Cyano" refers to the —CN radical.

"Hydroxy" refers to the —OH radical.

"Imino" refers to the =NH substituent.

"Nitro" refers to the —NO$_2$ radical.

"Oxo" refers to the =O substituent.

"Thioxo" refers to the =S substituent.

"Trifluoromethyl" refers to the —CF$_3$ radical.

"Alkyl" refers to a straight or branched hydrocarbon chain radical consisting solely of carbon and hydrogen atoms, containing no unsaturation, having from one to twenty four carbon atoms (C$_{1-24}$ alkyl). Long-chain alkyls include, for example, ten to twenty carbon atoms (C$_{10-20}$ alkyl), or ten to fifteen carbon atoms (C$_{10-15}$ alkyl). Short-chain alkyls include, for example, one to eight carbon atoms (C$_{1-8}$ alkyl), or one to six carbon atoms ($C_{1-6}$ alkyl), or one to four carbon atoms ($C_{1-4}$ alkyl). The alkyl radical is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be unsubstituted or substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (where t is 1 to 2), —$S(O)_tOR^{16}$ (where t is 1 to 2), —$S(O)_pR^{16}$ (where p is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Alkoxide" refers to a radical of —O-alkyl, wherein the alkyl is as defined herein. Examples of alkoxides include methoxide, ethoxide, propoxide (e.g., isopropoxide), butoxide (e.g., t-butoxide), pentoxide (e.g., t-pentoxide) and the like. A metal alkoxide can be a strong base, including, e.g., sodium t-butoxide, potassium t-butoxide, sodium t-pentoxide, or potassium t-pentoxide. A transition metal alkoxide may be a Lewis acid, including, e.g., titanium tetraisopropoxide.

"Alkenyl" refers to a straight or branched hydrocarbon chain radical consisting solely of carbon and hydrogen atoms, containing at least one C=C unsaturation, having from one to twenty four, or one to twelve carbon atoms, preferably one to eight carbon atoms or one to six carbon atoms, and which is attached to the rest of the molecule by a single bond, e.g., ethenyl (vinyl), allyl, butenyl, pentenyl, and the like. Unless stated otherwise specifically in the specification, an alkyl group may be unsubstituted or substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (where t is 1 to 2), —$S(O)_tOR^{16}$ (where t is 1 to 2), —$S(O)_pR^{16}$ (where p is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —$OC(O)$—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (where t is 1 to 2), —$S(O)_tOR^{16}$ (where t is 1 to 2), —$S(O)_pR^{16}$ (where p is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, halo, haloalkyl, haloalkenyl, cyano, nitro, aryl, aralkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 to 2), —$R^{15}$—$N=C(OR^{14})R^{14}$, —$R^{15}$—$S(O)_tOR^{16}$ (where t is 1 to 2), —$R^{15}$—$S(O)_pR^{16}$ (where p is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{16}$—$N(R^{14})S(O)_tR^{16}$ (where t is 1 to 2), —$R^{15}$—

N=C(OR$^{14}$)R$^{14}$, —R$^{15}$—S(O)$_t$OR$^{16}$ (where t is 1 to 2), —R$^{15}$—S(O)$_p$R$^{16}$ (where p is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxo-1,3-dioxol-4yl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, R$^{15}$—N(R$^{14}$)C(O)OR$^{16}$, —R$^{15}$—(R$^{14}$)C(O)R$^{16}$, —R$^{15}$—N(R$^{14}$)S(O)$_t$R$^{16}$ (where t is 1 to 2), —R$^{15}$—N=C(OR$^{14}$)R$^{14}$, —R$^{15}$—S(O)$_t$OR$^{16}$ (where t is 1 to 2), —R$^{15}$—S(O)$_p$R$^{16}$ (where p is 0 to 2), and —R$^{15}$—S(O)$_t$N(R$^{14}$)$_2$ (where t is 1 to 2) where each R$^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"Heterocyclylalkyl" refers to a radical of the formula —R$_b$R$_h$ where R$_b$ is an alkylene chain as defined above and R$_h$ is a heterocyclyl radical as defined above, and if the heterocyclyl is a nitrogen-containing heterocyclyl, the heterocyclyl may be attached to the alkylene chain at the nitrogen atom. The alkylene chain of the heterocyclylalkyl radical may be optionally substituted as defined above for an alkylene chain. The heterocyclyl part of the heterocyclylalkyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)S(O)$_t$R$^{16}$ (where t is 1 to 2), —R$^{15}$—N=C(OR$^{14}$)R$^{14}$, —R$^{15}$—S(O)$_t$OR$^{16}$ (where t is 1 to 2), —R$^{15}$—S(O)$_p$R$^{16}$ (where p is 0 to 2), and —R$^{15}$—S(O)$_t$N(R$^{14}$)$_2$ (where t is 1 to 2) where each R$^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"Heteroarylalkyl" refers to a radical of the formula —R$_b$R$_i$ where R$_b$ is an alkylene chain as defined above and R$_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Saponification" refers a process of hydrolyzing an ester in the presence of a base. Typically, the base may be a metal hydroxide. The solvent may be water or preferably an alcohol. When a metal hydroxide (e.g., potassium hydroxide) and an alcohol (e.g., methanol), the saponification process may be carried at a temperature below 50° C., or preferably in the range of 25° C.-40° C., or more preferably, in the range of 30-35° C.

Example 1

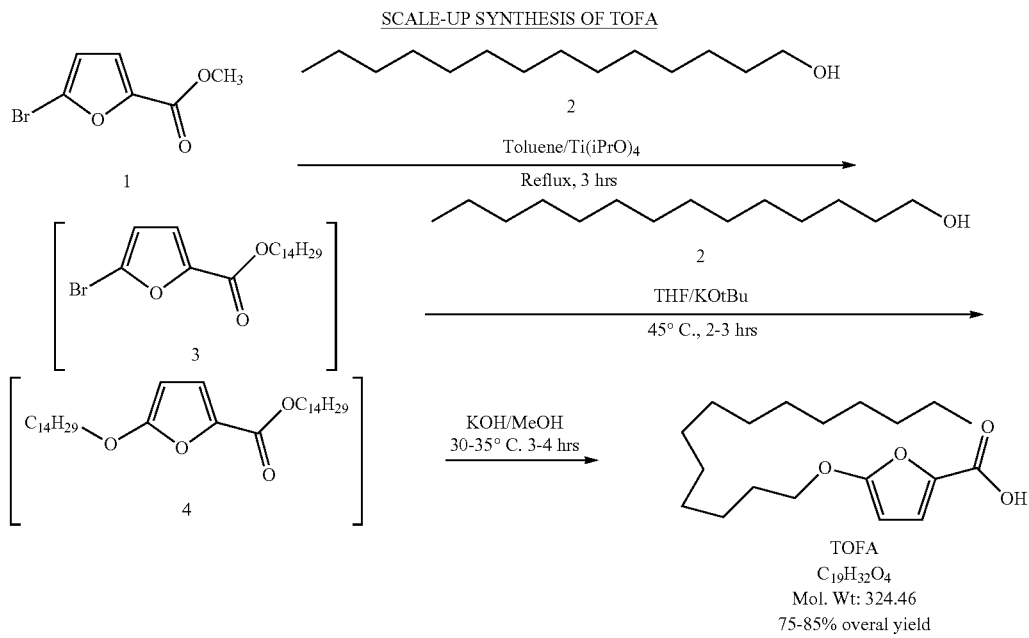

TOFA was prepared according to the above synthetic route. More specifically, methyl ester of 5-bromo-2-furoic acid (1) first underwent transesterification with 1-tetradecanol (2) (about 1 eq) in the presence of titanium tetraisopropoxide in refluxing toluene with removal of the methanol formed to provide tetradecyl ester of 5-bromofuroic acid (3). Thereafter, THF was added, and the transesterification product (3) was treated with tetradecoxide (i.e., potassium salt of tetradecanol 2), which was prepared by combining potassium t-butoxide or potassium t-pentoxide with tetradecanol.

Alternatively, an excess amount of 1-tetradecanol (e.g., 2.5 eq) may be used in the transesterification step, leaving about 1.5 eq of unreacted tetradecanol after the transesterification. Thereafter, potassium tetradecoxide may be formed in situ by adding potassium t-butoxide or potassium t-pentoxide to the reaction mixture containing the excess of tetradecanol.

Although sodium t-butoxide may also be used, it was observed that potassium t-butoxide was more soluble in THF. The reaction was carried out rapidly at a low temperature of 45° C. to produce mixed esters of TOFA, including predominately tetradecyl ester of TOFA (4) and about 5-10% t-butyl ester of TOFA (not shown).

Thereafter, the mixed esters were saponified by treatment with methanolic KOH for 3-4 hours at low temperature of 30-35° C. to produce TOFA in about 75-85% overall yield.

Advantageously, the intermediates (3) and (4) could proceed to the respective next step without being isolated. The above process reproducibly produced higher yields than the conventional process despite having two extra steps. In addition, the process could proceed at kilogram-scale (e.g., 27 kg or 48 kg) with consistent high yields.

All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

The invention claimed is:

1. A process for preparing a compound of Formula (I)

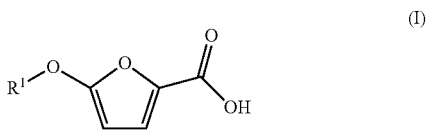

(I)

comprising:
converting a compound of Formula (II) to an intermediate compound of Formula (III):

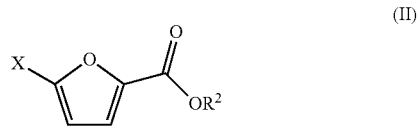

(II)

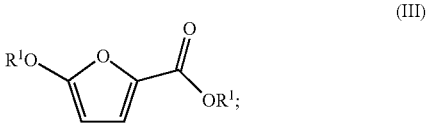

(III)

and
saponifying the intermediate compound of Formula (III) to form the compound of Formula (I), wherein, R¹ is alkyl, aryl, aralkyl, cycloalkyl, cycloalkylalkyl, heteroaryl, heteroarylalkyl, heterocyclyl or heterocyclylalkyl;

R² is $C_{1-4}$ alkyl; and

X is halo;

wherein converting the compound of Formula (II) to the intermediate of Formula (III) comprises:

transesterifying the compound of Formula (II) with R¹—OH to form an intermediate compound of Formula (IV)

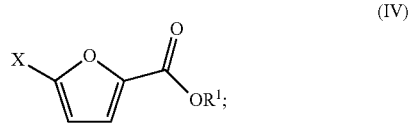

(IV)

and converting the intermediate compound of Formula (IV) to the intermediate compound of Formula (III) in the presence of R¹—OH and a base.

2. The process of claim 1 wherein R¹ is $C_{10-20}$ alkyl.

3. The process of claim 2 wherein R¹ is —$C_{14}H_{29}$.

4. The process of claim 1 wherein R² is methyl.

5. The process of claim 1 wherein X is Br or Cl.

6. The process of claim 1 wherein the base is characterized with having a conjugate acid having a pKa of at least 15.

7. The process of claim 1 further comprising removing R²—OH produced during transesterifying of the compound of Formula (II).

8. The process of claim 7 wherein the removal is carried out in the presence of a Lewis acid.

9. The process of claim 8 wherein the Lewis acid is titanium tetraisopropoxide.

10. The process of claim 1 wherein transesterifying of the compound of Formula (II) is carried out at a temperature below 120° C.

11. The process of claim 1 wherein converting the intermediate compound of Formula (IV) to the intermediate compound of Formula (III) is carried out at a temperature below 60° C.

12. The process of claim 1 wherein saponifying the intermediate compound of Formula (III) is carried out in the presence of a base at a temperature below 50° C.

13. The process of claim 12 wherein the base is a metal hydroxide combined with an alcohol.

14. The process of claim 13 wherein base is potassium hydroxide combined with methanol.

15. The process of claim 1 wherein the compound of Formula (I) is 5-tetradecyloxy-2-furoic acid.

* * * * *